United States Patent [19]

Gevins et al.

[11] Patent Number: 4,736,751
[45] Date of Patent: Apr. 12, 1988

[54] BRAIN WAVE SOURCE NETWORK LOCATION SCANNING METHOD AND SYSTEM

[75] Inventors: Alan S. Gevins; Nelson H. Morgan; Douglas S. Greer, all of San Francisco, Calif.

[73] Assignee: EEG Systems Laboratory, San Francisco, Calif.

[21] Appl. No.: 942,204

[22] Filed: Dec. 16, 1986

[51] Int. Cl.$^4$ ............................................... A61B 5/04
[52] U.S. Cl. .................................... 128/732; 128/731
[58] Field of Search ................................. 128/731–732

[56] References Cited

U.S. PATENT DOCUMENTS

| | | | |
|---|---|---|---|
| 4,094,307 | 6/1978 | Young, Jr. ........................... | 128/731 |
| 4,407,299 | 10/1983 | Culver ................................. | 128/731 |
| 4,632,122 | 12/1986 | Johansson et al. ............. | 128/731 X |
| 4,649,482 | 3/1987 | Raviv et al. ...................... | 128/731 X |

Primary Examiner—Kyle L. Howell
Assistant Examiner—Angela D. Sykes
Attorney, Agent, or Firm—Eliot S. Gerber

[57] ABSTRACT

A method and system is provided for the analysis of a human subject's brain wave activity on a statistical basis using a digital computer. The location of portions of the subject's brain and the location of at least 32, and for example 265, external scalp sensors are digitally recorded and stored in computer memory. The subject receives a set of stimuli which evoke brain waves (evoked potential EP or evoked magnetic fields EF) which, along with the location data, are statistically analyzed to indicate the brain sites giving rise to the activity. The brain site activity, and the time interrelationships of brain waves as they progress between brain sites, are displayed on a three-dimensional model or other three-dimensional perspective display.

35 Claims, 11 Drawing Sheets

FIG.I

FINITE DIFFERENCE MODEL

CLASSIFIER-DIRECTED ERP ESTIMATION
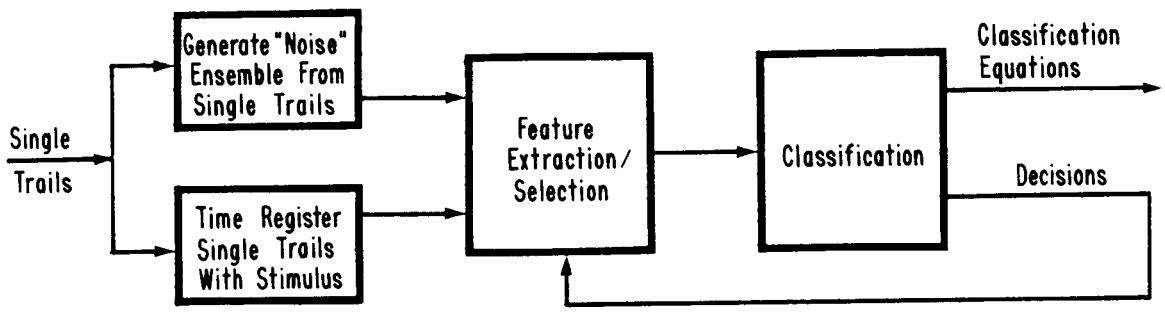
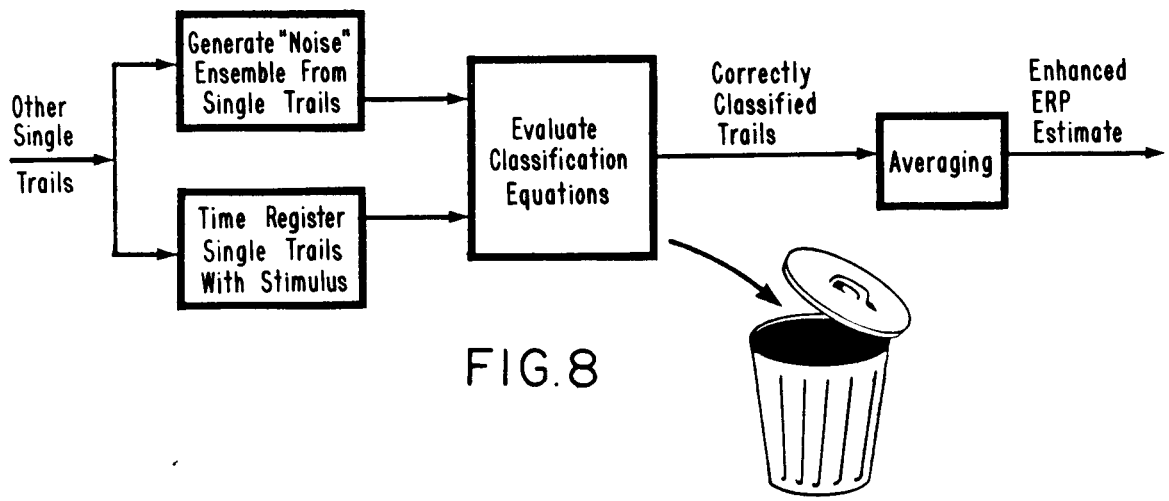
FIG. 8
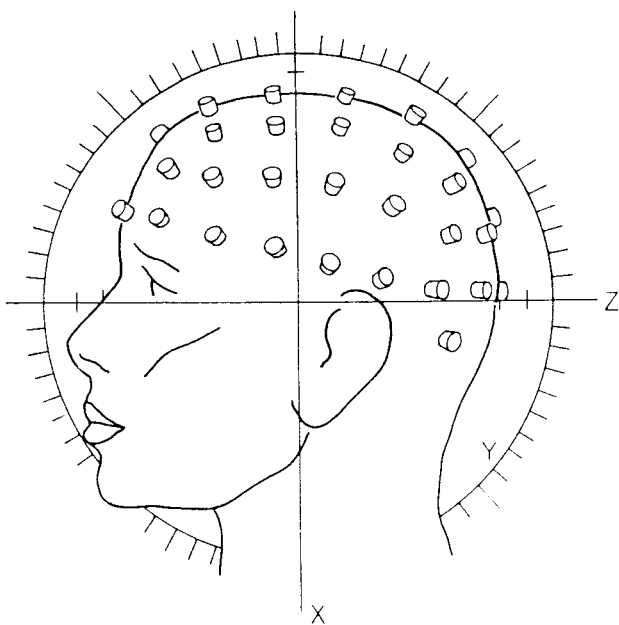
FIG. 10

COMPARTMENTALIZED
BRAIN MODEL

TABLE DRIVEN SOURCE MODELING

BRAIN WAVE SOURCE NETWORK LOCATION SCANNING METHOD AND SYSTEM

This invention was made with Government support under AFOSR Contract F49620-84-K-0008 awarded by the United States Air Force. The Government has certain rights in this invention.

BACKGROUND OF THE INVENTION

A number of scientific articles have been published regarding experiments directed to associating specific activity, such as vision, with specific areas of the human brain. Some of these experiments involve invasive techniques on animals, for example, the use of implanted electrodes or chemical dyes.

However, other studies have taken a different approach and have attempted to discover what happens in a person's brain when a person performs a task, like raising his finger, by placing electrodes or other sensors on or near the person's scalp. Those electrodes or sensors detect the tiny, microvolt or femtotesla level, electrical or magnetic activity at the surface of the scalp.

The detection of such faint brain wave signals is difficult because of the noisy electrical and magnetic environment created by hundreds of cars, electric lights, etc., etc. In addition, physiological "artifacts", which are electrical signals arising, for example, from scalp muscle activity or the eye blink of the subject, may produce an electrical and magnetic wave which is stronger than the subject's brain waves.

The detection and analysis of brain waves is even more difficult when the interest is in locating the specific three-dimensional sites giving rise to the waves and how the sites communicate with each other deep within the brain, as the subject responds to stimuli.

As an example of stimulus presentation, a subject is placed before a TV monitor. The letter "V" appears. If it slants to the left, the subject is to get ready to push a button with his left hand when a number appears on the monitor, and, if it slants to the right, he should get ready to push a button with his right hand. This is a simple task. But it has proven difficult to localize and display, in a readily comprehendable form, the dynamic brain wave activity ("mass neuroelectric processes") which give rise to the subject's ability to recognize the stimuli, i.e., to recognize the "V" and the subsequent number (cognitive behavior) and to physically react (perceptumotor), i.e., move his hand.

There are not now presently commercially available any non-invasive methods or systems which will locate selected brain sites, and display what occurs at those sites in response to stimuli and responses, in an accurate three-dimensional appearing display.

SUMMARY OF THE INVENTION

In accordance with the present invention, there is provided a method and system to detect, store, analyze and display a subject's brain waves, called "MAN SCAN", for a mental activity network scanner, FIG. 4.

A large number of electrode sensors, at least 32 and as many as 256, are placed proximal to the scalp of the subject, preferably using a hat. In other systems, for example, conventional electroencephalographic (EEG) recording, it is usual to use only about 20 electrodes. Each electrode is connected, through a low-noise high-gain amplifier, to an analog-to-digital multiplexer system which converts the subject's faint analog brain waves into digital data. The three-dimensional positions of the electrodes are measured with a digitizer which records their positions and stores their positions in computer storage. A magnetic resonance image (MRI) of each subject is also recorded and the electrode sensor positions are mathematically registered, in computer storage, with the scalp in the MRI image. A computer-controlled set of adaptive tasks are presented to the subject in order to extract functional source network patterns. These tasks preferably include: a bimanual (two-hand) visuomotor task (hand response to a picture) with and without load on short-term memory; an auditory-visual visuomotor task, such as the subject's moving his finger when he hears a specific word, or sees the correct picture on the TV monitor; an auditory monitoring task with varying load on short-term memory; temporal sequencing task; and a linguistic battery. The electroencephalographic (EEG), and, optionally magnetoencephalographic (MEG), brain waves and eye movement (EOG) data are scanned for noise contaminants, such as muscle artifacts, by several different layered-network statistical pattern classifiers. Then, on-line, a technician uses interactive computer graphics to check the borderline trials and eliminate those with too much noise. Using a statistical pattern classification algorithm, the signal-to-noise ratio can be further improved by eliminating individual trials which lack strong event related signals. Bandpass digital filters are then applied to further enhance event related signals of interest.

The data are now free of contaminants and have a satisfactory signal-to-noise ratio in each trial. However, the EEG data are still spatially blurred (out of focus), and must be further processed prior to spatial analysis. Consequently, spatial deconvolution analysis is applied to the EEG data to reduce the distortion of the brain waves due to their transmission through the cerebrospinal fluid (internal brain fluid), skull and scalp. The spatial deconvolution analysis is based on a finite-difference model of the brain and head. When there are fewer than 64 electrodes and the distance between electrode sensors is greater than 3 cm, an optimal estimate of the Laplacian operator in two dimensions can be substituted for the deconvolution.

"Functional relationships" between sensors are next computed on averages obtained from the enhanced, filtered, deblurred EEG or MEG data. The functional relationships are computed as the lagged crosscovariance over fraction-of-a-second intervals time registered to a stimulus or to a response. The EEG or MEG current distributions and the crosscovariance information are then displayed in a three-dimensional appearing perspective display, preferably in color, which shows stimulus and response-related "functional relationships" between sensors at each of a number of time intervals.

The data, at this step in the method, have not yet been processed to determine whether the brain waves reflect near surface brain activity from the immediately underlying areas, from distant near surface areas, or are derived from sites deep within the brain. Therefore a source network localization analysis is performed. This involves using linear-least-squares analysis to determine the optimal match between the brain wave fields observed at the scalp and the fields produced by different combinations of model sources. Either EEG or MEG field measurements, alone or in combination, can be used in this analysis. A finite-difference model of the subject's brain and head is constructed from magnetic resonance image scans, and then the model is divided up into discrete compartments for the source network localization analysis. The source network analysis is repeated for each of a number of successive time points during the interval used for functional relationship analysis, and a dynamic programming technique is used to select the best source network from a number of possible candidate networks. The selected network is then validated on an independent sample of data.

The final results of these analyses are displayed in a three-dimensional appearing perspective display, preferably in color, which shows the selected sites in the source network, and the pattern of their functional interrelationships, which best account for the brain waves observed in response to the stimuli and responses.

BRIEF DESCRIPTION OF THE DRAWINGS

The following detailed description should be taken in conjunction with the accompanying drawings, in which:

FIG. 8 is a block flow diagram showing the classifier-directed ERP estimation;

FIG. 10 is a side view of the model head showing the location of the sensors;

DETAILED DESCRIPTION OF THE INVENTION

A. Active Electrode EEG Hat

An active electrode EEG helmet 10 is placed on the head of the subject.

Figure 1:
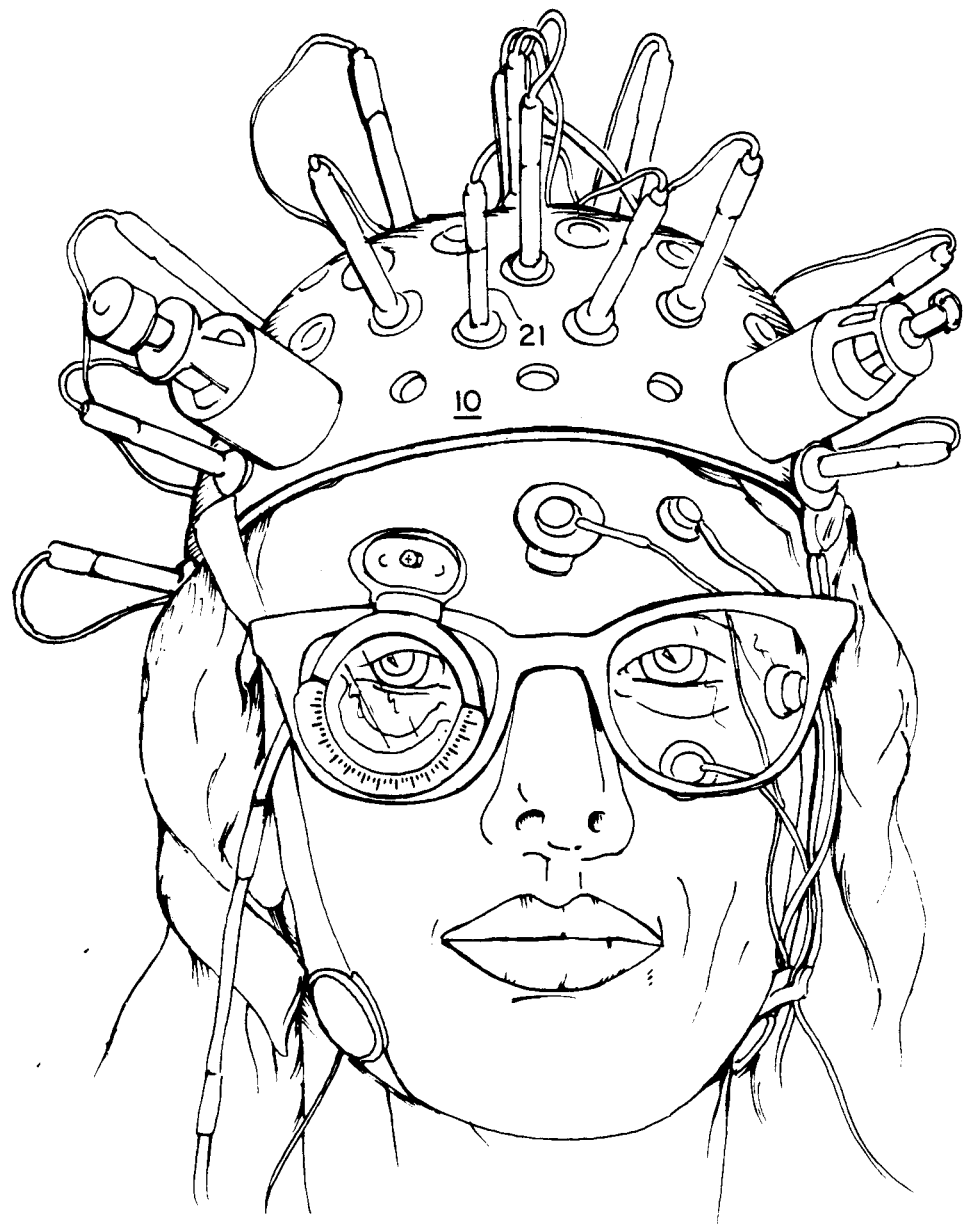
FIG. 1 is a front plan picture of the electrode hat on a human subject.

As shown in FIG. 1, preferably the helmet 10 is a rigid helmet having 32 to 256 spring-loaded/barrel tin disk electrodes 21. Each tin disk has a protruding, tapered 2-mm-long nub. The hat 10 is held down with a double chin strap. Several back-and-forth lateral motions of the helmet, made with the outstretched hand over the front, back, and each side of the head causes the protruding electrode nubs to part the hair and make contact with the scalp of the subject.

The helmet shown in FIG. 1 carries at least 32 and up to 256 electrode sensors 21 which make electrical contact with the scalp with little or no preparation of the scalp. The hat employs CMOS integrated circuits for low-noise amplification, filtering and multiplexing of the faint brain wave EEG signals.

Figure 2:
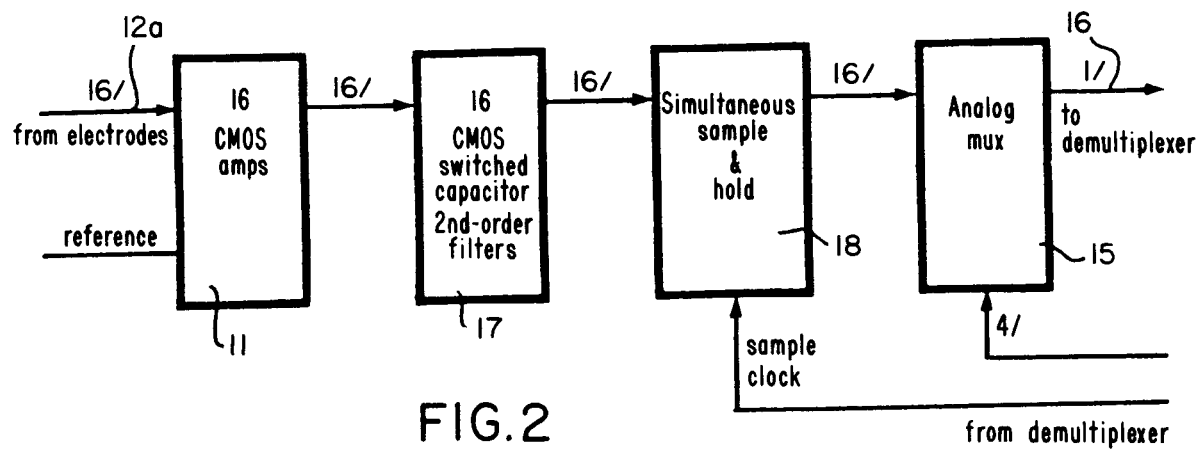
FIG. 2 is a block circuit diagram of the circuitry, including an analog multiplexer, which may be connected to the sensor electrodes.
Figure 3:
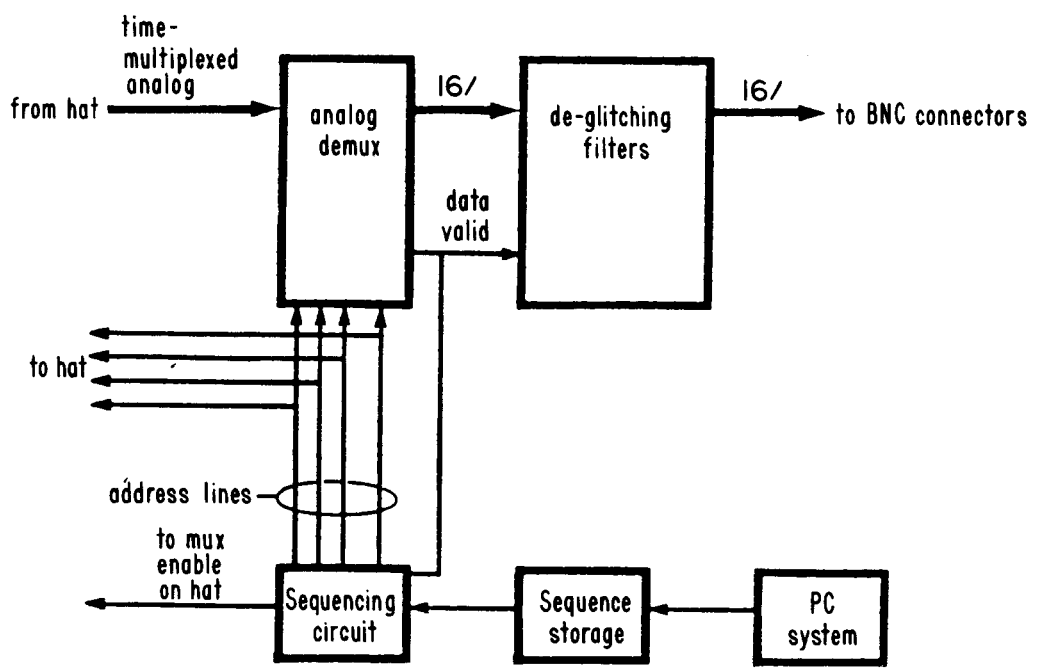
FIG. 3 is a block circuit diagram of the demultiplexing board.
Figure 4:
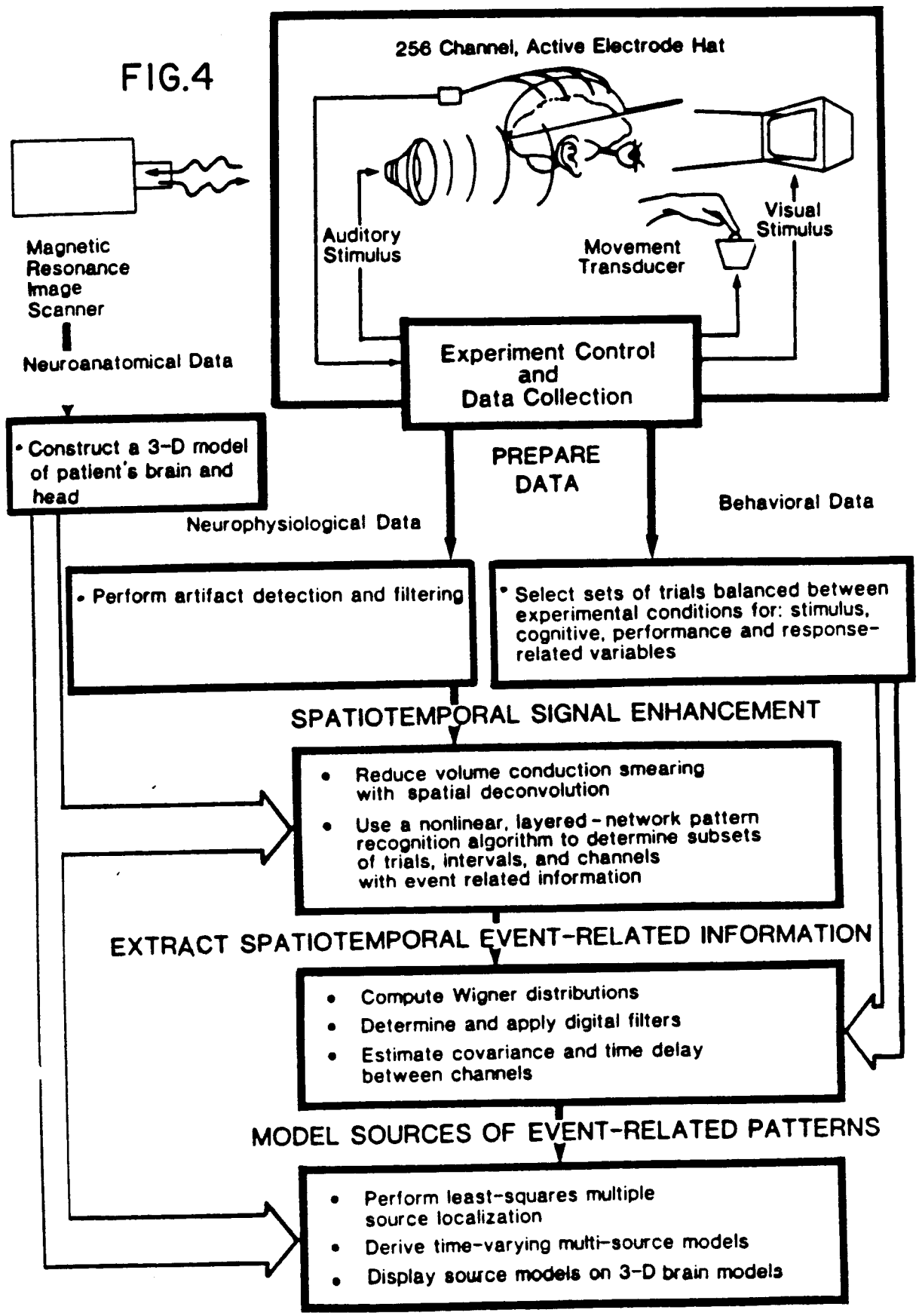
FIG. 4 is a block flow diagram of the apparatus and steps of the method of the present invention.

The circuitry shown in FIG. 2 is preferably built into the hat 10, which requires that electronics for each group of 16 channels be implemented with a custom integrated circuit. If active circuitry is placed off the hat, commercially available IC's may be used. As shown in FIG. 2, "CMOS amps" 11, is a group of 16 operational amplifiers employing Complementary, Metal-Oxide-Silicon (CMOS) electronic circuitry. Each amplifier input is connected to one of the electrodes 21 by lines 12a–12n. The amplifiers provide gain of about 1000 over a frequency range of 0.01 to 100 Hz. An additional programmable gain of 1–50 is provided at the chip output. Chopper-stabilized amplifiers are used for low noise. The CMOS amplifiers are chosen for their low power drain (so that batteries may be used), and also to permit high impedance electrode contact with the scalp. The amplifiers are compensated to move the closed-loop gain to 100 Hz, which acts as the first stage of antialiasing. The second stage of antialiasing is a 2nd-order switched capacitor filter 17 for each channel. The output of each filter 17 is sampled and held at a suitable global sampling rate, 256 Hz, by a simultaneous sample and hold circuit 18. A final stage on each chip (or board, for the off-hat implementation) is the 16 - to - 1 analog multiplexer 15. Four bits of address select the amplifier on each chip, and 4 bits of address select one of up to 16 chips, for a total of 256 possible channels. This time-multiplexed analog output is used as an input to a console demultiplexing board, (see FIG. 3), which derives 16 analog channels from each multiplexed line. This output is useful for hats with 32-64 channels, and provides compatible signals for other analog devices. The preferred integrated circuit (IC) embodiment for higher channel capability, not shown, employs a delta-sigma A/D on each chip of the hat; resulting in a one-bit digital output from each helmet chip in addition to the analog output. This output will have much better noise immunity in unshielded environments.

B. Electrode Position Measurements

The top and base position of each electrode is measured, recorded and stored in computer storage in three dimensions, using a three-dimensional digitizer, such as the "Perceptor" (TM Micro Control Systems, Connecticut). The digitizer places the three-dimensional shapes of objects into conventional digital data (ASCII code) with an accuracy and resolution of 0.007 in (0.018 cm).

The digitizer includes a table on which a padded holder for the subject's head is secured. An arm is mounted on top of the digitizer. The user takes the arm and moves its pointer to each spot whose position he wants digitized. The arm has 5 pivot points which allow for maximum flexibility. Potentiometers housed in the joints transmit electrical information about the angles of rotation of each segment of the arm as they pivot on the joints. This angle information is automatically translated into XYZ spatial coordinate input data (ASCII Code).

The subject rests his head in the padded headholder for the approximate ten minutes required to digitize the positions of all the electrodes of the helmet 10, for example, even with 256 electrodes ten minutes should suffice. From this information as to the three-dimensional electrode positions and the known length of electrodes, the scalp location of each recording electrode tip is calculated by the computer, for example, a Masscomp 550 computer.

C. Positions of Cranial and Cortical Structures

Figure 5:
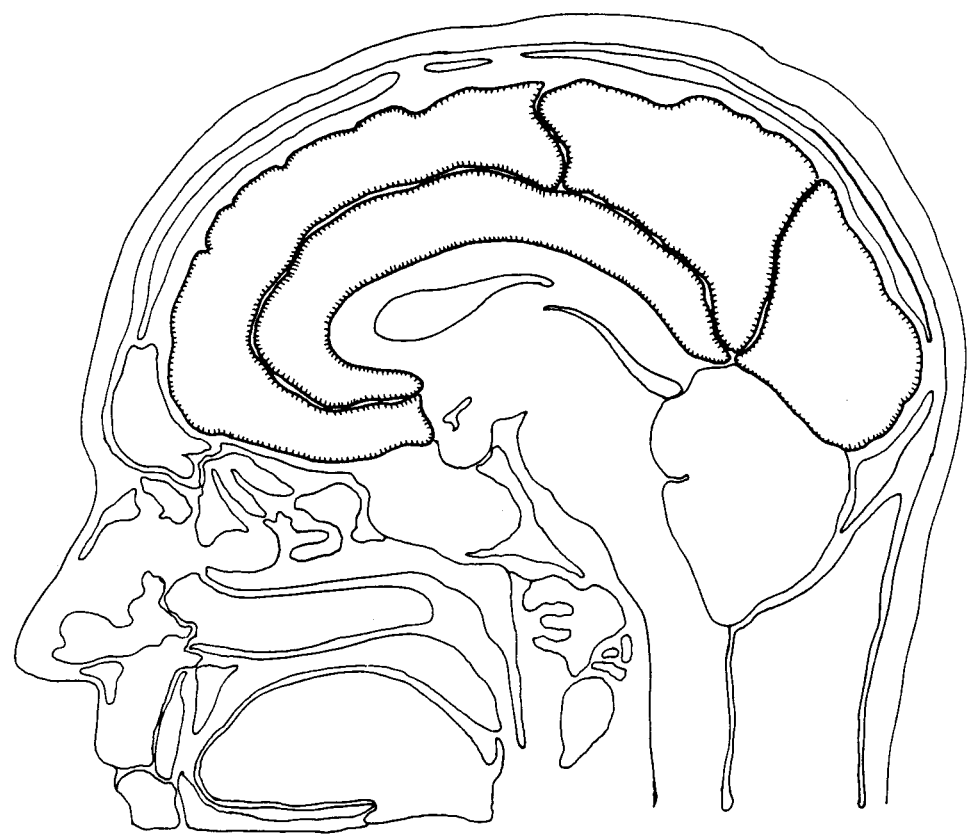
FIG. 5 is an MRI image of a human brain with sites of interest outlined.

A full set of clinical magnetic resonance image (MRI) images is obtained for each subject before the helmet is placed on the subject. These are high-resolution (0.95 mm pixel), 3-axis (coronal, sagittal and transverse) images of the head of each subject which show a cross-section of the proton density at sections as little as 3 mm apart over the whole volume of the head. The MRI tapes are read into the computer and displayed on a color graphics terminal. Certain head areas of the stored MRI images ("loci") are digitized to give coordinate surfaces for the scalp, the outer and inner surfaces of the skull, and cerebral surface, as well as the loci of the major fissures (e.g., Sylvania, central, longitudinal, calcarine), see FIG. 5.

All MRI images contain an inherent non-linear distortion which can arise from several sources and may vary in magnitude and proportion depending on a number of parameters. MRI distortion correction can be divided into two parts, (1) distortion measurement and characterization and (2) image correction. Before correction, this distortion is measured using phantoms with known physical dimensions. The position of the electrode sensors is marked by placing small oil (vitamin A or E) capsules on an identical helmet which is then placed on the scalp. The capsule locations are clearly seen in the MRI image as characteristic white regions, and those capsule locations correspond to the locations of the electrodes with which they are associated.

A major source of image distortion arises from the inhomogeneity of the magnetic gradient coils of the MRI imaging system. However, a non-uniform static field can also result in a disparity between the true and observed object positions. A characterization of the image deformation due to changes in the repetition time (TR) and echo time (TE) parameters is made in addition to analysis of object dependent and object independent error. Time stability of the imaging system is typically tested by comparing reference MRI with those made during the lasat system recalibration.

Image correction requires fitting a spline to the empirically measured or predicted distortion function. For each image the actual and observed object positions define a two-dimensional grid of points which characterizes the distortion. A smooth surface spline which interpolates each of the grid points is then constructed. Finally the distortion is corrected by mapping the image through the inverse of this function using any of several well-known image transformation algorithms.

D. Registration of Coordinates for MRI, EEG and/or MEG

Figure 6:
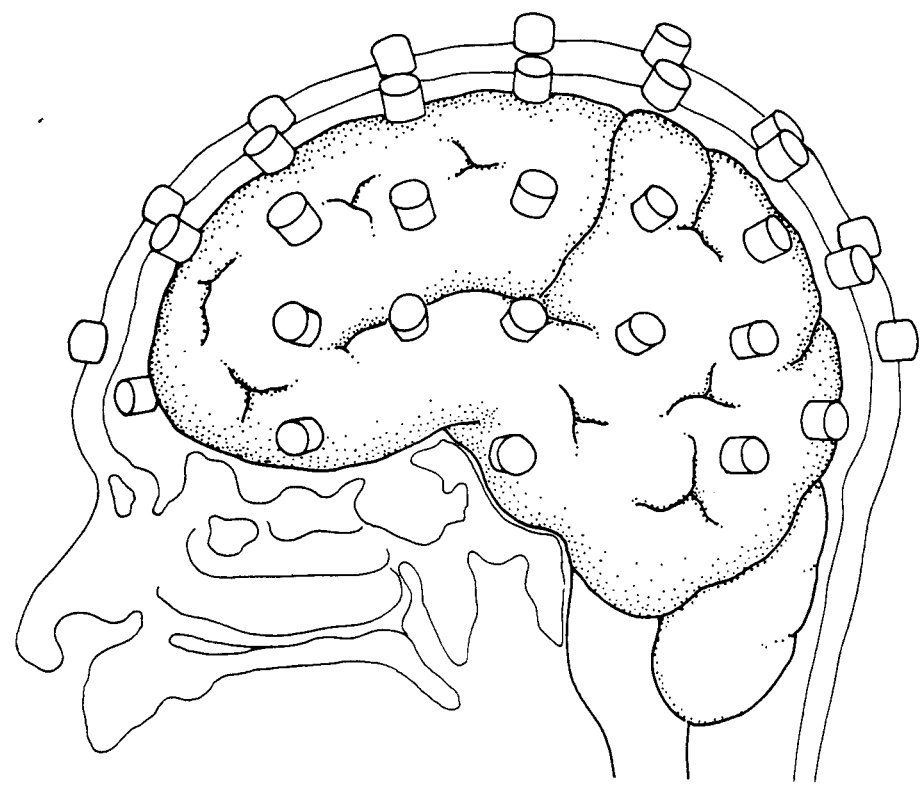
FIG. 6 is an MRI image of a human brain showing sensor locations on the scalp.

After correcting the distortion, the MRIs are registered with the EEG and/or MEG data. The positions of known external fiducial marks (inion, nasion and external pre-auricular notch) are determined in the MRI, EEG and/or MEG coordinate systems (FIG. 6). When the position of at least three identical points is known in each of the coordinate systems, the remaining data points can be registered with a simple translation and orthogonal rotation.

This procedure produces estimates of the scalp surface points derived from the EEG and/or MEG electrode sensor positions and the MRI. Numerical comparison of these estimates then provides the transformation (scaling, rotation and translation) required to take one set of digitized coordinates into the other. This allows a double-check on the accuracy of positioning using the fiducial markers.

The magnetoencephalograph (MEG) is an alternative system to the EEG to detect brain waves.

The weak magnetic fields from the human brain may be detected and mapped using a cryogenic "SQUID" (superconducting quantum interference device). The brain activity evoked by sensory stimuli produces weak magnetic fields in the order of 0.1 pT (picotesla). The resolution is limited by the size of the pick-up coil; however, significant variations in the magnetic field of the brain have been observed at distances of 1 cm, see Williamson, Brenner and Kaufman, *Biomedical Applications of SQUIDSs* (ISSN: 0094-243X/78/106/1.50 Am. Inst. of Physics, pages 106–116, 1978), incorporated by reference herein. The SQUID senses the magnetic field using a superconducting flux transporter whose detecting coil, because of its windings and geometry, is relatively insensitive to uniform background fields generated by uniform sources.

E. Computer-Controlled Adaptive Tasks To Test Higher Brain Functions

After the helmet 10 is placed on the head of the subject, he is presented with a set of tasks, in which he is asked to voluntarily move some portion of his body in response to a stimulus which he receives, such as a picture or sound.

1. Bimanual Task. This task measures the subject's preparatory processes, visual stimulus processing, response execution and updating to feedback about the accuracy of his performance. In this task the subject is instructed to fixate on a point at the center of an amber CRT monitor of a graphics processor, monitor type USI EV-2131A, which is positioned 70 cm directly in front of his eye. He waits for a visually presented response hand cue, for example, the letter V, slanting to the left for a left-hand response and slanting to the right for a right-hand response. The duration of the picture is 125 msec. The characters on the monitor screen have an illumination of 0.5 log fL. One second later the stimulus is presented on the CRT monitor having a duration of 125 msec. The characters subtend a visual angle of under one degree, also slanting to the left for a left-hand response or to the right for a right-hand response. A random 22% of the trials are miscued, i.e., cued for a left-hand response and with stimulus for a right-hand response, or vice versa. The subject is told to withhold response, not move his hands, on the miscued pictures. If he moves his hands on a miscued picture, the feedback shows an "XX" and he is penalized for that trial.

In this set of trials, the subject is instructed to respond to the stimulus, i.e., the picture on the monitor screen, without hesitation with a ballistic flexion of his right- or left-hand index finger on a modified Grass Force Transducer, exerting a pressure corresponding to the stimulus number of a linear scale of 1 to 9. For example, if the picture is left 5, he should respond with medium pressure with his left index finger. A two-digit feedback number, of 125 msec duration, indicating the exact force applied (to one-tenth of a unit) is presented on the monitor screen to the subject 1 sec. after his peak response pressure. Trials are randomly ordered in blocks of 20, except that the first two trials are not miscued. The subject initiates a block of 20 trials by pressing a button and the 20 trials follow automatically under computer program control, at inter-trial intervals of 1.5 seconds. If the subject does not respond within 1 sec. after the stimulus, his response is ignored and the feedback is presented to the subject on the monitor screen 2 sec. after the stimulus, indicating his non-response. After each block of trials, a report appears on the CRT monitor showing the average response accuracy for right and left hands separately, the number of incorrect responses to miscues and the number of "bonus points".

2. *Visuo-Motor and Auditory Motor Memory Tasks.* These tasks, called "working memory load tasks", test the subject's immediate working memory and perceptuometer coordination. Preferably there are three different memory load tasks presented to each subject, namely: (1) the Visuo-Motor Monitoring Task, null memory condition (VMMT, 0-back); (2) the Visuo-Motor Monitoring Task, memory load condition (VMMT, 2-back); and (3) an Auditory Monitoring Memory (AUM) Task.

The VMMT is designed to allow precise control of stimulus parameters, load on immediate working memory, motor activity and eye movements. Stimuli consist of single-digit numbers (125 msec duration) presented on the CRT monitor screen as in the Bimanual Task. Subjects respond on each trial with a ballistic flexion of their right index finger on a Grass Force Transducer with a pressure proportional to the stimulus number on a linear scale from 1 to 9. The feedback number, shown after each trial to the subject on the monitor screen, is underlined if the response is sufficiently accurate. Accuracy is based on an adaptive error tolerance, the geometric average of the error (the distance from the required response pressure) on the previous five move trials. The inter-trial interval is 1.5 sec., during which a fixation symbol (X) is on the screen.

The two memory load conditions in the VMMT are: a null memory or 0-back condition, in which the required response pressure is indicated by the current stimulus number; and a 2-back memory condition, in which the response pressure is indicated by the stimulus number which was given two trials back. In other words, the subject is told not to respond to the current number or the number before, shown on the screen, but rather to the number which appeared two trials back. In order to add a recognition element to the tasks and also to avoid overly short response times in the memory task, 20% of the trials in both conditions are designated as catch-trials in which the subjects are not required to respond during these trials. In the 0-back condition (response to current number) the no-move catch-trials are those in which the stimulus number is 0. In the 2-back condition, catch-trials are designated as the occurrence of a stimulus number identical to the 2-back stimulus number.

The AUM (Auditory Monitoring Memory) task consists of a 2-back (or 3-back) memory load condition. In this task, the subjects are asked to respond whenever the current stimulus is the same as the number two (or three) trials back. Stimuli consist of single-digit numbers from 245 to 430 msec, spoken by a voice synthesizer, such as the Votrax (TM) synthesizer, and presented in blocks of 50. The interstimulus interval varies randomly from 4 to 5 seconds. Stimuli are presented over two speakers, which are located in front of the subject. As in the VMMT tasks, the subjects respond by pressing on a force transducer with the forefinger of their right hand. In the AUM task, unlike the VMMT, the response is registered as either on or off, and there is no feedback or warning signal for individual trials. Subjects receive visual feedback, by viewing the CRT monitor screen, at the end of each block of trials, showing: (1) targets (catch-trials) hit; (2) targets missed; (3) false positives; (4) average reaction time; and (5) standard deviation of reaction time.

3. *Sequencing Task.* This task is designed to test the ability of the subject to temporally integrate and manipulate sequences of stimuli and produce sequences of motor responses. In this task, the subject sits facing a graphics terminal and waits for the appearance of a small "X" at center screen. The "X" signals the start of a trial and serves as a visual fixation point. The stimulus sequence begins 1 second later. The sequence consists of 3-8 dots of light, 125 msec duration, presented at the rate of 4 per second. Each dot subtends a visual angle of 0.25 degree, and can appear in one of three positions: at the center, 0.5 visual degree to the left, or 0.5 visual degree to the right. During a pretesting training period the subject learns to associate right-hand index, middle and ring fingers with left, middle and right stimulus positions, respectively. Two hundred fifty msec after the last stimulus, an imperative symbol, a triangle of duration 125 msec, is presented at center screen.

The task is to execute a sequence of finger presses on three switches under index, middle and ring fingers of the right hand, evenly timed and as close to the stimulus presentation rate as possible (4/sec). In the "forward" condition (upward triangle) the subject is to execute a sequence of finger movements corresponding to the stimulus series. In the "backward" condition, inverted triangle, he is to execute the sequence in reversed (retrograde) order. The fixation point remains on the screen until the feedback interval in order to help the subject fixate his eyes. The feedback display, presented 500 msec after completion of the last response to the subject, shows the expected sequence on top with the sequence actually produced by the subject just underneath. At the end of every block of 15 trials, a report is shown with the percent of correct reponses, and a performance goal which must be exceeded in the next block to win a bonus. In order to maintain a constant level of challenge, the number of dots in the sequence automatically increases as a moving average function of the subject's performance during the preceding five blocks.

4. *Language Tasks.* A series of three language tasks measures the brief, time-varying neurocognitive patterns of the subject's basic phonemic, lexical and grammatical processes. The tasks involve: (1) matching phonemic stimuli divorced of sematic content (e.g.,/sen-/and/cen/) versus stimuli comprised of letters which do not form a phonemic sound (e.g., xkj); (2) identifying homonyms (e.g., more and moor) versus antonymic contrasts (e.g., old and new); and (3) assessing the grammaticality of simple sentences on the basis of number, subject-verb and tense agreement.

During these language tasks, the stimuli are presented on a CRT monitor screen, or over loudspeakers, as in the other tasks. The subject responds by pressing contact switches with his right hand, index and middle fingers. A warning cue precedes the first stimulus by 1 sec., and the second stimulus is presented 1 sec. after the first stimulus. The inter-trial interval is 2 seconds. Trials are presented in blocks of 20 randomly ordered task types. There is an equal number of match and mismatch trials. After each block of trials, a performance score report is provided, as described above.

F. Artifact Rejection

Since the brain waves are so faint, at the microvolt or femtotesla level, it is important that the recorded data be as free as possible from noise contaminants called "artifacts".

Figure 7:
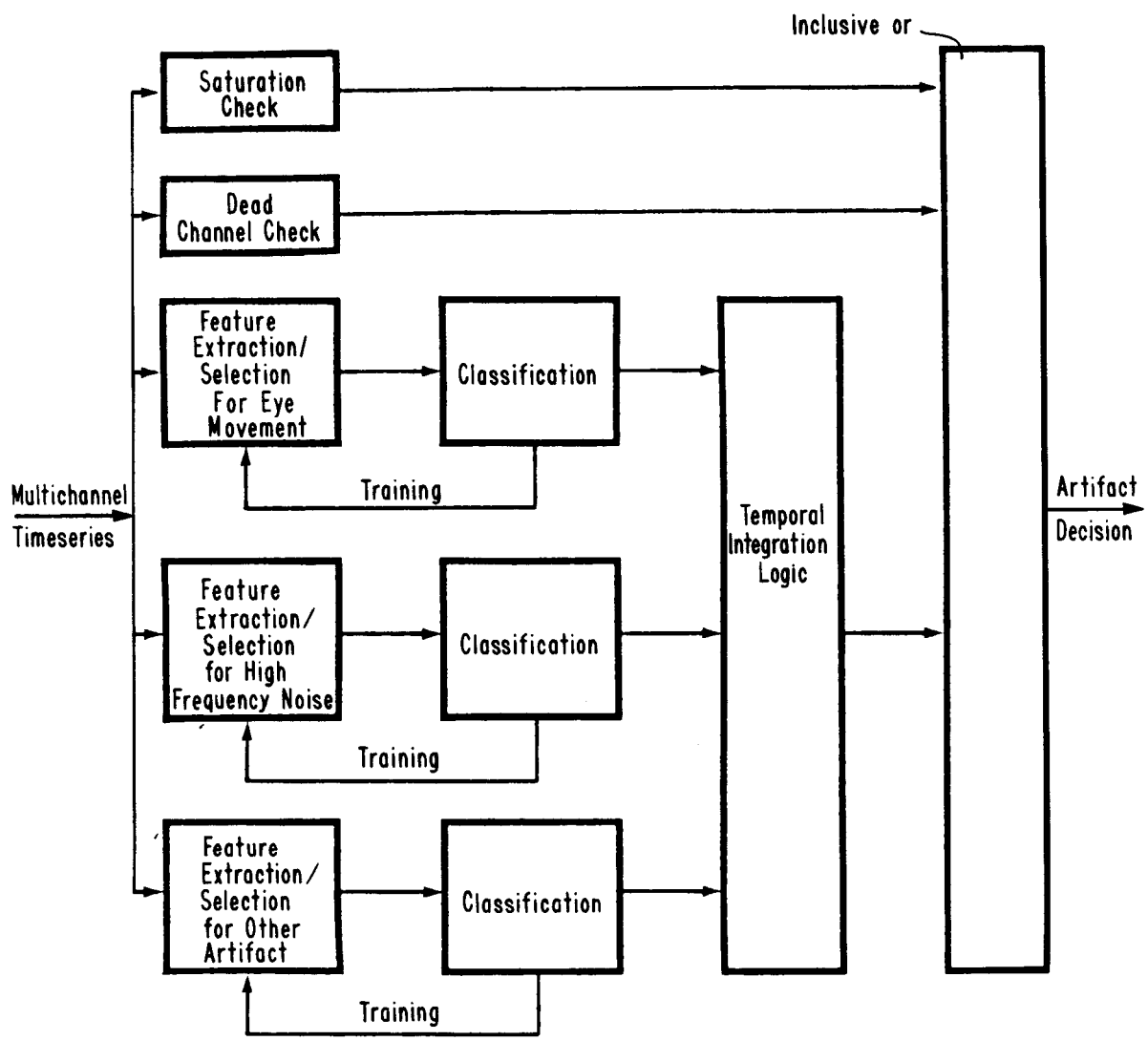
FIG. 7 is a block flow diagram of the classifier-directed artifact detection.

In order to reject various types of artifacts, on-line programs check for dead or saturated channels, monitor the subject's eye movements, and delay the start of each trial until the systems's amplifiers have recovered from artifacts. When a run of 100 trials is completed, it is subjected to an automated artifact analysis using the computer under control of a computer program, i.e., "software". The artifact detection software detects and labels artifacted segments of single-trial time series. In particular, programs check for vertical and horizontal eye movement, eye blinks, dead or weak channels, saturated channels, and muscle potential contamination or other high-frequency noise that has significant energy in spectral regions of interest, see FIG. 7. These software programs use a combination of time domain and frequency domain features for classification by multiple 2-layer pattern recognition machines. Parallel detectors are each specialized for a different type of artifact. Simple amplitude detectors are sufficient ot detect dead channels and amplifier saturation. A layered-network pattern classifier uses low-frequency power spectral density, cross spectral density with horizontal and vertical eye movement channels, and a correlation coefficient with the vertical eye movement channel as candidate features for eye blinks and movement. Another classifier uses power spectral density, zero-lag auto-correlation, and the first-order autoregressive (AR) predictor coefficient as candidates for muscles and instrumental artifact. An optional third classifier uses the same features for other types of artifact that users wish to train the machine to reject. Features are evaluated over half-second intervals every 125 msec of the time series. Classification decisions are made automatically by the computer, every 125 msec, using a nonlinear interpolation of neighboring decisions. Labeled segments (artifact or no artifact) are used for each training class to train the computer to distinguish artifacted segments, and an equal number for each test class. An interactive graphics trial editing program is used by an operator to check the classification decisions of the computer program. Artifacts that are recoverable are filtered out, e.g., non-saturating eye-blink are filtered out using least squares noise cancellation with reference electrodes near the eyes; environmental MEG noise is filtered out using least squares noise cancellation with reference sensors more than several centimeters away from the head.

G. Reduction of Volume Conduction Effects Using Spatial Deconvolution

Figure 7A:
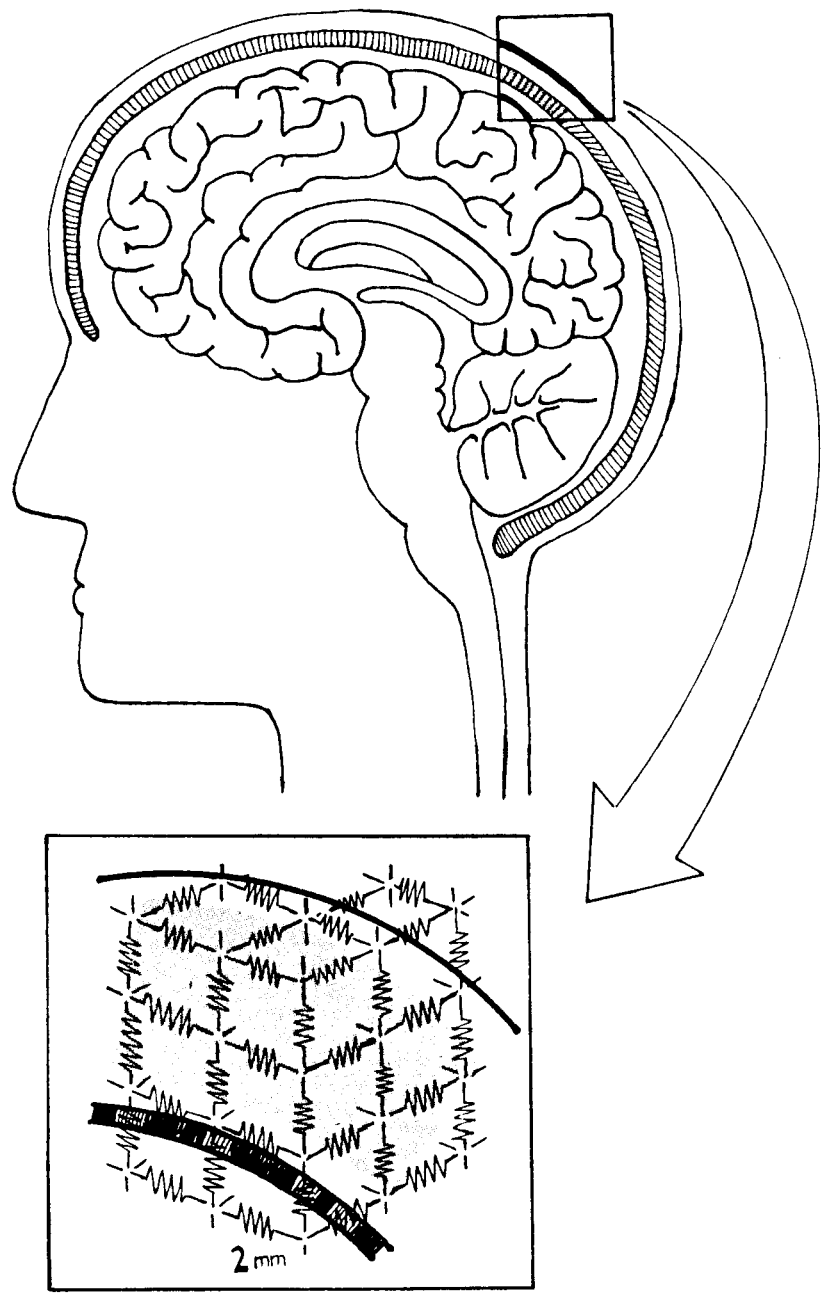
FIG. 7A is a diagram showing the finite difference model of the brain.

1. Overview. An "image" of the brain wave electrical current normal to the surface of local cortical areas is achieved by using spatial deconvolution methods to reduce volume conduction and increase spatial resolution. Finite-difference methods are used to represent the true geometry of the subject's brain cortex, cerebrospinal fluid, skull and scalp, and the passive transmission of currents into the skull and then to the surface of the scalp is modeled, FIG. 7A. This operation is performed without imposing an arbitrary source generator model; the number(s), position(s), or orientation(s) of possible sources are not identified. The finite-difference approach to modeling the head hasa the advantage that the discretization can be performed with a grid of points which can be uniform for each coordinate direction. This procedure admits a simple interpretation in which the brain is viewed as an electrical circuit. The circuit consists of a network of equivalent resistors whose connecting nodes are the "uniform sampling points" of the model.

In the finite-difference implementation, the normal currents entering the skull are calculated, by the computer, from the observed brain wave potentials at the electrode sensors using piecewise linear approximations to the electrical properties of the skull and scalp regions. A finite difference form of the Laplace equation for a sourceless volume yields Kirchoff's Current Law at a network node. Using a 3-D reconstructions of each subject's head from MRI sections as stored in computer memory, the equivalent resistive network for the skull and scalp is derived by the computer software. Given certain restrictions on its topology, a sourceless resistive network with known voltage outputs can be uniquely solved for the entering currents. Those entering currents are the brain waves produced at each of the selected brain sites.

Solution of the system node equations takes several seconds on a Masscomp 550 computer for 10,000 equations (nodes) and a sparse matrix frontwidth of 12, using sparse Gaussian elimination. This yields a transformation matrix which is stored in computer memory and which is then applied to each distribution of measured potentials, to derive the strength of the currents entering and exiting the subject's scalp.

2. *Conductivity Measurements in the Model.* A three-dimensional appearing model, which may be viewed in perspective view, is used as the analog or constructed twin of the subject's brain and head. The ratios of conductivities in the model is determined by measuring the scalp potential distribution produced largely by a single compact population of neurons, represented as a current dipole, whose location is approximately known in the subject's brain. A steepest-descent, non-linear, least-squares fit between the measured potentials and the forward solution of the finite-difference problem is performed by the computer softward. The unknown parameters include the ratios of conductivities of the tissues, as well as the dipole strength, and any parameters of the dipole position and orientation left undetermined by anatomical knowledge gained from the MRI pictures. The absolute conductivities are not determined from this measurement because the absolute strength of the "equivalent dipole source" modeling this population is not known.

There are a few brain sites which (i) produce a distinct picture and location on the MRI scan, and (ii) produce distinct and recognizable brain waves when stimulated. For example, the brain waves which are produced by the somatosensory evoked potential peak at 20 msec produced by mild stimulation of the contralateral median nerve at the wrist is a highly localized, discrete source. It is generated by a single tangential dipole in the hand area of somatosensory area 3b. This dipole is located 2.5–3.0 cm below the surface of the scalp. Since the locus of the central sulcus is known from the MRI pictures, a single parameter of position along the central sulcus is all that is required to determining the position of the activated dipole. In addition to approximate locus and depth, published values of the amplitude of the cortical potentials are also of use in constraining the solution. Only a single parameter of dipole orientation is required, since the dipole may be considered perpendicular to the sulcus and only its degree of tilt into the sulcus is unknown. In a model with 3 conductivity layers, there are only 5 parameters being 2 conductivity ratios and 3 dipole parameters (including dipole strength). Using up to 256 scalp electrodes and an enhanced average evoked potential with a high SNR, an optimal or near-optimal solution for these 5 parameters can be computed.

Another known compact source is produced by a stimulus at 1 degree to the right or left of the visual fixation point. This is mapped into a more-or-less radial (posterio-lateral) dipole in the contralateral occipital pole. The subject is shown, as a stimulus, on the CRT monitor, a vertical constrast reversal sine wave grating, confined to a semi-circular area in either the right or the left visual field. This type of stimulation produces a steady-state response produced by a single current dipole in the contralateral primary visual area. If two parameters of orientation and one of dipole strength are allowed, the two conductivity ratios again make five parameters in the fit.

Recordings for these parameters are made at the end of the recording session after the active task data have been collected. About 100 trials of each somatosensory and visual stimulus are collected.

H. SNR Enhancement

1. Overview. Since brain waves are faint electrical or magnetic signals, and the brain waves of interest which are related to a particular stimulus or response may be obscured by other activity in the brain, it is important to improve the amount of stimulus—or response-related brain wave signal and decrease the non-stimulus—or response-related "noise," i.e., improve the signal-to-noise ratio (SNR). The SNR can be improved by simple averaging of all trials or, optionally, by averaging only trials selected for a high SNR. This selection is done with minimal assumptions about signal characteristic using a statistical pattern classifier to choose those trials which are discriminable from a synthesized noise process with statistics very close to those of actual data (FIG. 8), see Gevins, et al, 1986, EEG Clin. Neurophysiol., 66: 177–186, incorporated by reference herein. Then, time and frequency bandpass filter to further enhance the selected data are determined, optionally, with the aid of Wigner distributions see Morgan & Gevins, 1986—IEEE Trans. Biomed Eng. BME-33(1) 66–70, incorporated by reference herein. Filters are implemented with minimum Heisenberg product (bandwidth x timewidth) designs. Between-channel covariances and other "functional interrelation" measures are computed on enhanced averages of the resulting filtered sets of (selected) single trial multivariate time series. Filtering, as well as the trial selection, can be modified by feedback from classifier performance. This is called "classifier-directed" filtering, see Gevins and Morgan, 1986, IEEE Tr. Biomed. Eng., BME-33, (12), incorporated by reference herein. The chosen filter provides an optimality criterion of maximal discriminability between time series with signal (high SNR) and time series without signal (low SNR). A noise process synthesized from the recorded data, as in the trial selection method, is used for the latter time series.

2. Steps in SNR Enhancement a. Create an artifact-free data set, from each subject's stimulus-and-response-registered data. They will be compared with a reference "baseline" data set, computed from the same data without stimulus-or-response-registration, in order to select trials with consistent event-related signals.

b. Compute average stimulus-registered (and response-registered when appropriate) event-related time series (ERTs) for each subject. Use the latencies of chosen peaks in each person's averaged ERT time series to determine the centerpoints of analysis windows for trial-selection analysis, see Gevins et al, Electrical Potentials, etc., *Science* 213, pgs. 918–922 (1981) and Neurocognitive Pattern, etc. *Psychophysiology* 22, pgs. 32–43 (1985), both incorporated by reference herein. Adjust the widow size to span the peak (usually 125 to 250 msec). Set other windows at stimulus and response times.

c. Apply a low-pass filter to the time series which reduces power by 3 dB at 7 Hz and by 12 dB at 12 Hz; then decimate. Use 3–7 time series values as features. Partition the data of the two condtions (event-related data and noise) into three training and non-overlapping validation sets.

d. For each channel, apply a layered-network pattern recognition algorithm (a type of discriminant analysis), see Gevins et al EEG Patterns etc., *Clin. Neurophysiol.* 47, pages 693–703 (1979), incorporated by reference herein, to generate equations which represent invariant differences between the event-related and non-event-related conditions in the current training data set at the interval chosen. Test the equations with the validation data to determine which electrodes differ significantly between conditions.

e. Repeat step "d" (above) for each training and validation data set and compute the mean validation set accuracy. Set the level of significant classification well above the level attained with the data randomly assigned to two pseudo-conditions, which are determined by a separate analysis. Draw diagrams showing which electrodes contain significant task-related information in each interval.

f. Collect trials with task-related signals (i.e., trials correctly classified in the validation set). Compute "enhanced" averaged ERTs (and Wigner Time-Frequency Distributions; see Morgan & Gevins (1986), cited infra), using those signal-bearing trials which attained significance in a majority of the channels. Graph ERTs, amplitude distributions over time intervals and Wigner Distributions.

I. Spatial Synchronization ("Functional Interrelationship") Measures

1. *Overview.* Several methods measure "functional interrelationships" of low-frequency, event-related brain signal time series as a first step in characterizing the human brain's distributed processing network. This approach is based on the hypothesis that when areas of the brain are functionally related, there is a consistent pattern of waveshape similarity between their brain waves, i.e., predictability of the brain wave recorded at one area at a particular time by that of other area(s) at earlier times to which it is functionally related. In previous implementations, this amounted to measuring time series correlation between pairs of channels on sets of single-trial data (Gevins et al., 1981, 1984, 1985, infra) Simpler and more robust computational procedures have now been developed for measuring the magnitude and time delay of "functional interrelationships" from enhanced, filtered event-related, averaged timeseries. These methods, which are collectively referred to as "event-related covariances" include: (1) optionally applying statistical pattern recognition methods for selecting trials with consistent event-related signals in order to form the enhanced averages (see Section H, and Gevins et al, 1986, cited infra); (2) determination of bandpass filter characteristics for the averages from Wigner (time-frequency) distributions, see Morgan & Gevins 1986, cited infra, and/or by classifier-directed filtering, (see Gevins & Morgan, 1986 cited infra); (3) computation of crosscovariance functions between averaged enhanced, filtered timeseries within brief (125–400 msec) intervals centered on event-related waves; (4) determination of the significance of the covariance by Monte Carlo statistical studies; and (5) the use of 3-D perspective color graphics to display the pattern of significant covariances, for example, on model heads or 3-D brain models reconstructed from the MRI scan.

Figure 9:
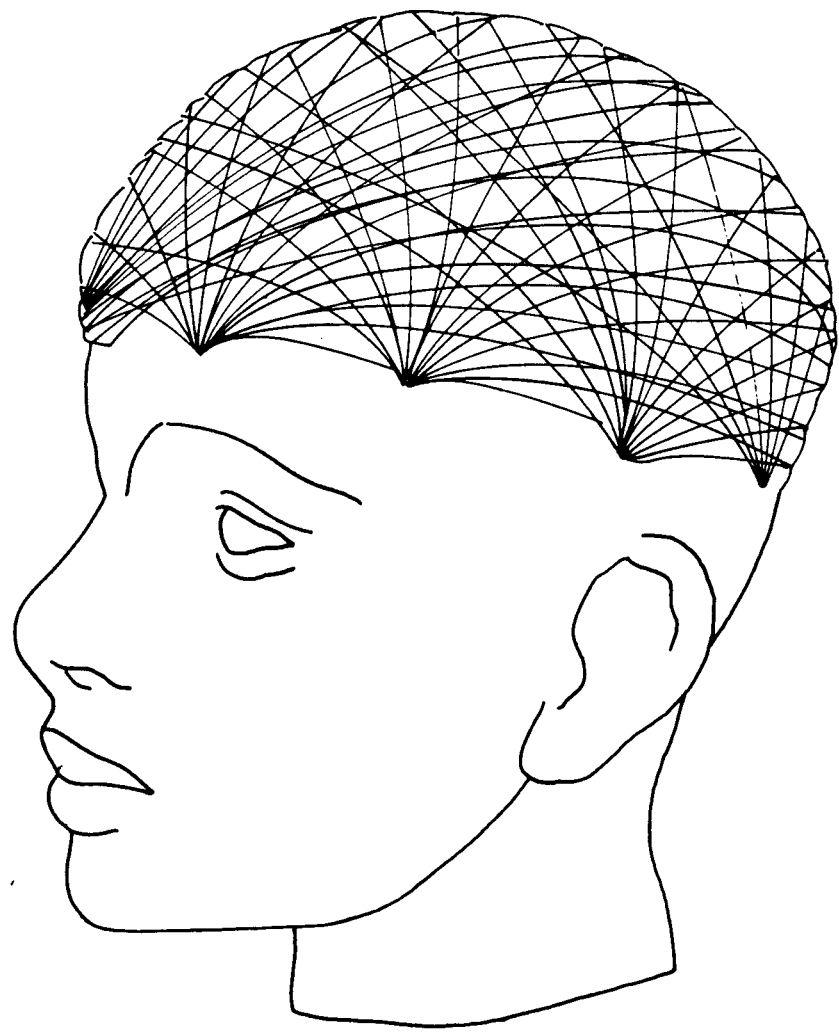
FIG. 9 is a perspective view of the model head showing all possible pairs of functional interrelationships projected onto the scalp.

2. Steps in computing event-related convariances.

a. Select digital filters and intervals for measurement of between-channel covariances by examining results of step "f" of SNR enhancement.

b. Compute multilag crosscovariance functions between all pair-wise channel combinations of the enhanced, filtered and decimated averages in each selected analysis window, see FIG. 9. Use the magnitude of the maximum crosscovariance function and its lag time as "functional interrelationship" features.

c. Determine the significance of the crosscovariance features. This requires an estimate of the standard deviation of the "noise covariance, which is obtained as follows: Random intervals in each single trial of the ensemble are averaged. The covariance analysis is performed on the filtered and decimated version of the resulting averages, yielding a distribution of "noise" covariances.

d. Graph the most significant covariances in each interval. The most significant covariances are the top standard deviation(s) of the observed covariance distributions.

e. Test the ensemble of significant covariances for a difference between experimental conditions.

For all significant covariances in either of the two conditions, compute the standard error and do a t-test between means. Measure similarity between multivariate covariance maps with an estimate of the correlation between them. Calculate these estimates using a distribution-independent "bootstrap" Monte Carlo procedure, which generates an ensemble of correlation values from randomly selected choices of the repeated measures. This will also yield a confidence interval for these estimates.

J. Three-Dimensional Perspective Graphics

1. *Overview.* 3-D graphics display the location and appearance of objects in space as seen from an arbitrary viewpoint. The display is computed, by the computer software, as follows: A linear transformation in homogeneous coordinates, contained in a single four-by-four matrix, is used to represent any combination of rotation, translation, scaling and perspective transforms. Using this as a basis for transforming points is space, these points or vertices are combined to form edges and polygons. Brightness values are coupled based on an ambient lighting model and the polygon surface normals. Smooth surfaces are generated by interpolating the intensity values across each surface. Combining this with a hidden surface removal algorithm, a realistic image of any collection of polygons can be constructed.

Figure 10B:
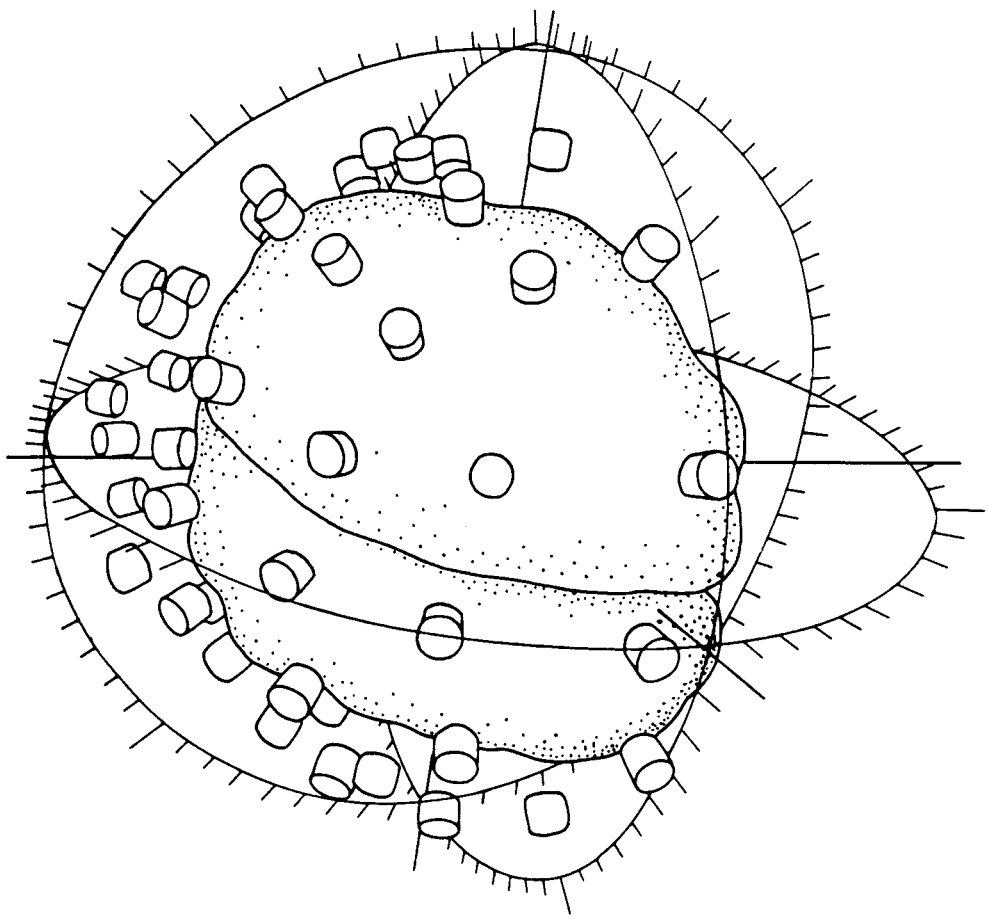
FIG. 10B is a three-dimensional perspective model of a subject's brain constructed from his MRI scans.

2. *Model head construction.* The electrode sensors are marked in their normal positions on a mannequin head. Additional reference points are marked and numbered over the remainder of the head. A list of polygons, in computer memory, of the computer graphics system, is then created where each polygon consists of a polygon ID number followed by an ordered list of reference points which make up the vertices of the polygon. Computer graphic calculations require that the polygons' surface be oriented by listing the vertices in a counterclockwise direction as viewed from the outside of the head. The resulting collection of vertex positions and polygon lists is stored in a "display file" which can be read and displayed by the graphics display program, FIGS. 9 and 10.

Figure 10A:
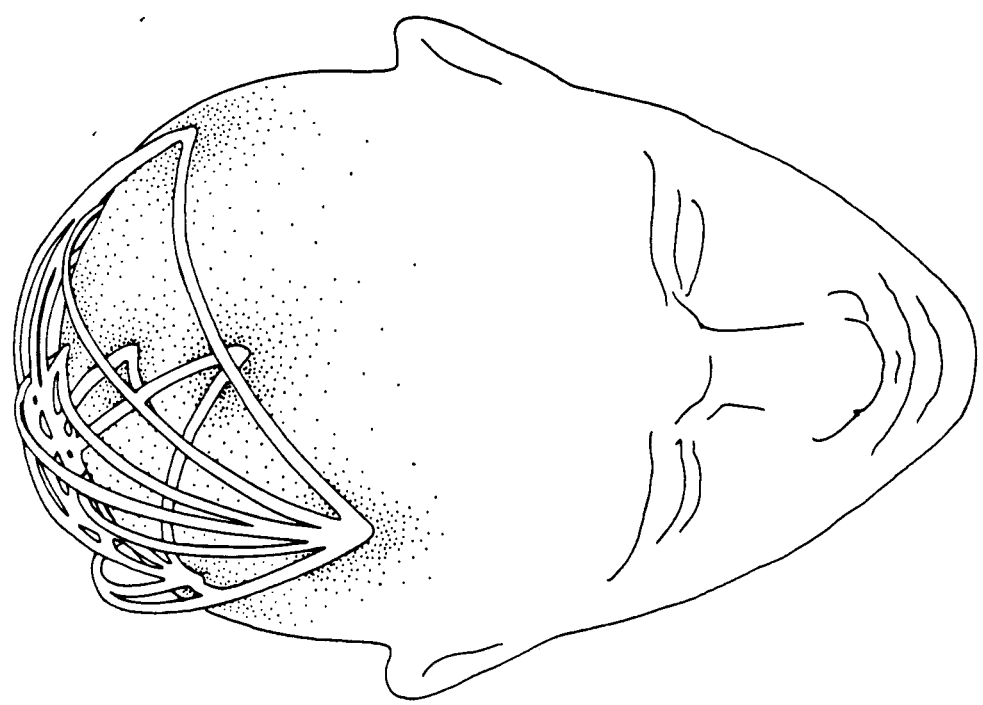
FIG. 10A is a perspective view of the model head showing only the significant functional interrelationships while right-handed subjects prepare to perform a visuomotor task.

Event-related covariances, and current distributions from single subjects or groups of subjects are displayed on the model head using the following preferred conventions, see FIG. 10A. The thickness of a line is proportional to the significance of the covariance. The color of a line indicates the time at which the two channels are maximally synchronized (yellow: 0–15 msec; green: 16–31 msec; blue: 32–27 msec; red: 48–79 msec; purple: 80 msec). The arrow points away from the channel that is leading in time. The arrow is the same color as the line when the two convarying channels are positively related. A gray arrow indicates that the covarying channels are negatively correlated. The current distribution of currents exiting and entering the scalp on a flame scale in which a maximal entering currents are purple and maximal exiting currents are red.

3. *MRI reconstruction.* Magnetic resonance images are used to provide the spatial locations of the surfaces of areas within the brain. Preferably the data provides ten or more sagittal, ten or more coronal and ten or more transaxial (horizontal) views of each subject. Each greyscale image is displayed on a color graphics computer workstation and the contours of interest, i.e., the internal brain areas which are selected, are traced, by the operator, using the mouse tracking device, see FIG. 5. The screen coordinates of the cursor are translated to the corresponding image position, which is then used to compute the location within the magnet. Inherent in each MRI image is a spatial error which is introduced in the MRI process. By correlating the fiducial selectrode sensor markers from the MRIs, described above, with the scale electrode sensor positions which are independently measured with an XYZ position transducer, described above, an error estimate is obtained. This estimate is used to provide a error correction for the internal brain contours described above. The corrected contours are used to generate a set of triangles which cover the exterior surface outlined by the contours of interest. Finally, the sagital coronal and transaxial reconstructions are combined to form a single computer graphic image, see FIG. 10B.

K. Source Localization

1. *The Problem:* Given an adequate model of the tissue of the head, a knowledge of the positions, multipole character, orientations, and magnitudes of the sources of the brain electrical potential and magnetic fields is sufficient to determine the measured potentials and fields at the scalp. Since the potentials may be considered quasistatic the spread of the potential is governed by Poisson's equation:

$$\overline{\nabla} \cdot (\sigma \overline{\nabla} \phi) = I_V$$

where $\phi$ is the potential, $\sigma$ is the conductivity tensor, $I_V$ is the volume current source density. Considering only isotropic models, in regions free of sources, this reduces to Laplace's equation.

$$\overline{\nabla} (\sigma \overline{\nabla} \phi) = 0$$

Unfortunately, a knowledge of the potentials and fields at the scalp does not suffice to determine the sources. A given distribution of potential (field) at the scalp, i.e., the brain generating sites, or any other surface including the sources, may be produced by infinitely many different distributions of sources. In order to resolve this ambiguity, some additional information as to the character, orientation, and/or number of sources must be added to determine the sources of a given potential (field) distribution. Preferably the sources are modeled, in a computer software program, as one or a few equivalent current dipoles whose positions and orientations are unconstrained in a concentricsphere model of the tissue. However, while one or two equivalent current dipoles may be adequate to model the major source of a sensory ERP peak, such as the reaction to a light flash, such models do not seem realistic for even simple goad-directed tasks. Furthermore, the nonspherical topology of the subject's brain may result in considerable distortion of the results.

2. *Overview of solutions:* More realistic head and brain models, as well as additional information, are required to attempt multi-source localization. A number of steps are applied to achieve these requirements: (1) use of MRI scans and finite-difference models to improve the head and brain model; (2) increased spatial sampling using up to 256 scalp electrodes; (3) reduction of spatial smearing of scalp potential measures with improved Laplacian operators or finite-difference spatial deconvolution; (4) use of other signal processing procedures to. enhance the SNR; (5) use of event-related covariances of deblurred EEGs, and optionally MEG fields, to constrain the errors in source modeling; (6) use of several algorithmic approaches, including an exhaustive search for a subset of physical sources from a larger candidate set; and (7) validation of the source models on independent data.

Figure 11:
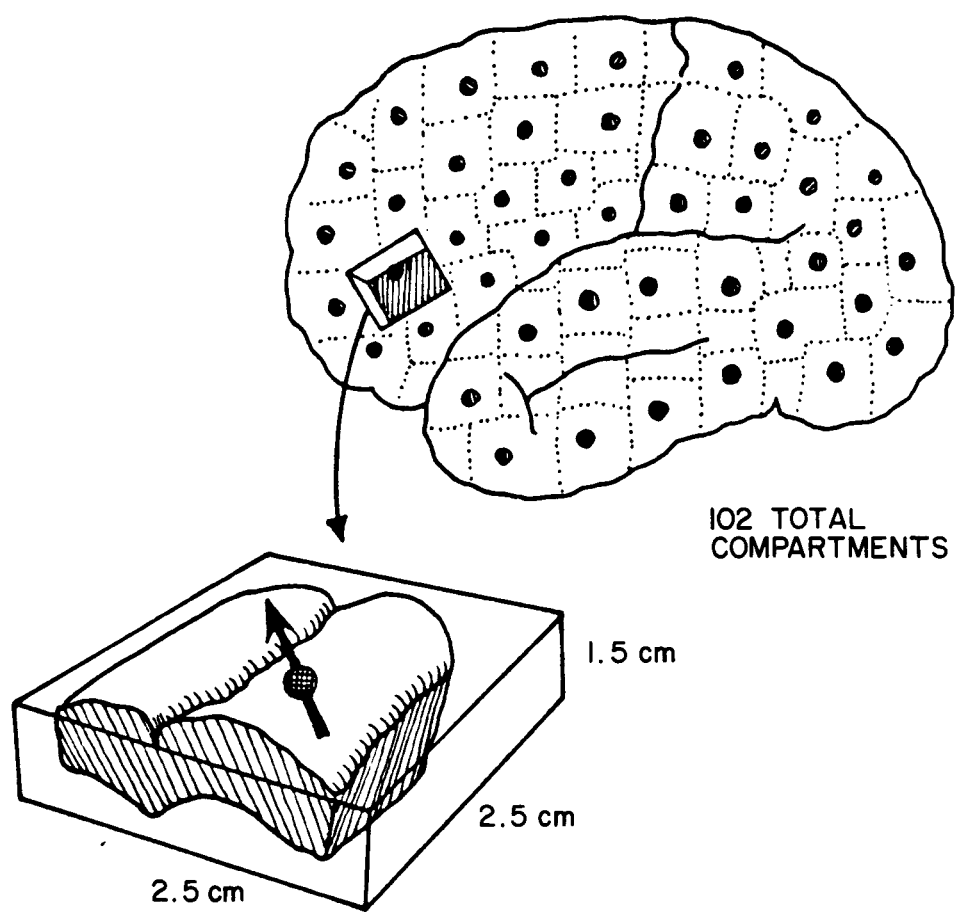
FIG. 11 is a perspective view illustrating the compartmentalized brain model.
Figure 12:
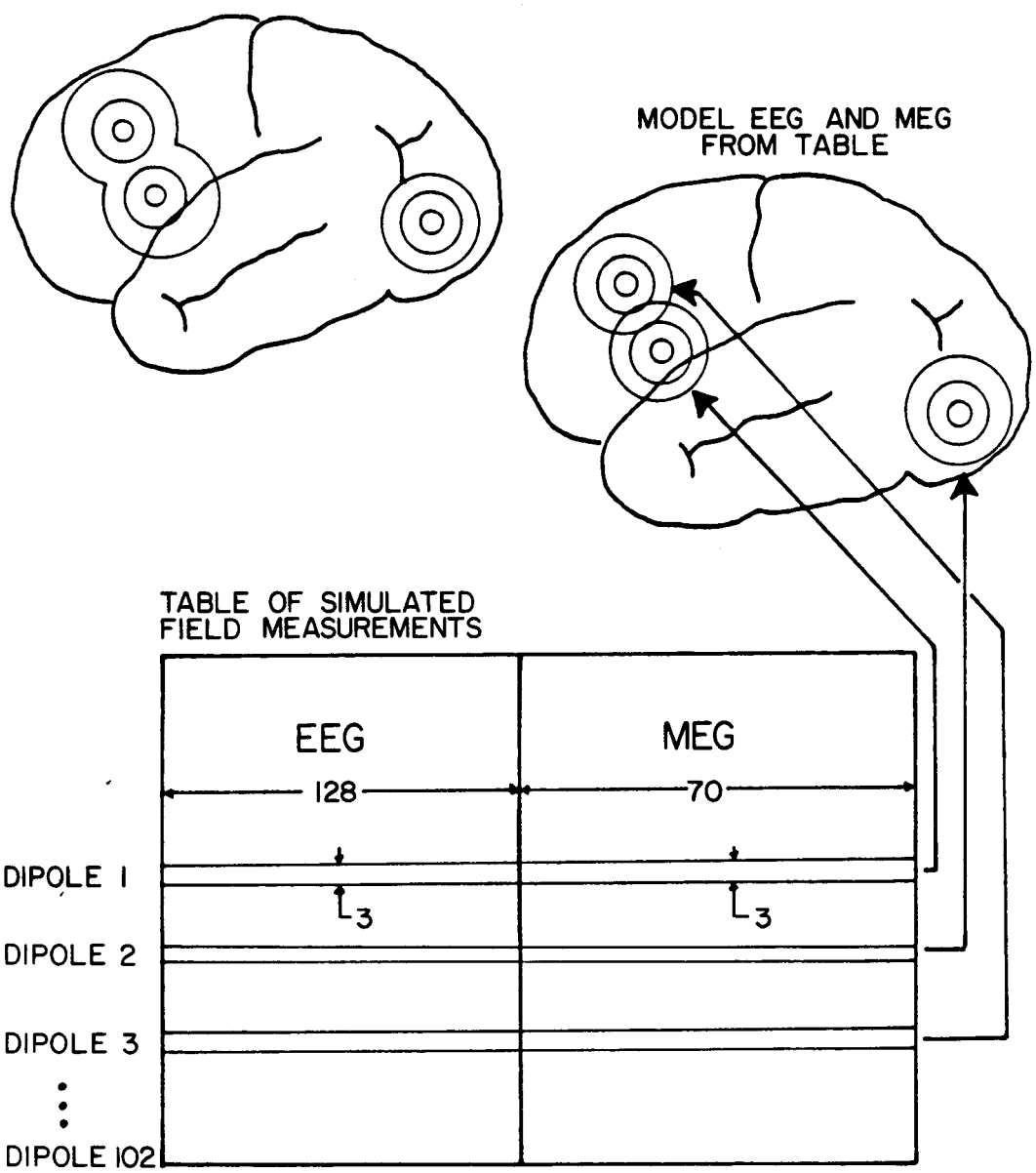
FIG. 12 illustrates table-driven source modeling.

3. *Use of several algorithmic approaches.* The finite-difference (resistive network) approximation described above is extended to source modeling. The resistive network represents the scalp, skull, cerebrospinal fluid, and the brain itself. Both cortical and subcortical sources are postulated in least-squares minimization methods described below. Resulting brain currents throughout the network are calculated. The calculated branch currents entering the skull predict the normal current density due to each source.

a. *Unconstrained nonlinear least squares.* The historical approach to source localization has been to posit the number of sources and then compute all 6 parameters (5 for MEG) of each equivalent dipole using a least-squares adaptive minimization search. In this approach, source configurations are assumed and perturbed to minimize the sum of squared errors between predicted and observed potentials. "Steepest descent" adjustment parameters can be calculated by setting to zero estimates of the partial derivatives of the sum of squared errors with respect to each parameter. Ultimately, the procedure should converge to a local minimum of error (i.e., to a point for which any incremental parametric adjustment results in an increase of squared error). Unfortunately for such constrained nonlinear optimization procedures, there is no guarantee that any local minimum found is also a global minimum. That is, there may be other sets of parameters which better represent the data. This problem is especially bad for unconstrained highly dimensioned problems, such as the problem of the identification of brain wave generating sites.

b. *Constrained Linear Least Squares.* A brain model is posited with a restricted number of compartments (roughly 100) corresponding to major cortical areas and relevant subcortical systems, FIG. 11. The approximate location of compartments is determined from each subject's MRI scan. Each compartment is represented by 3 orthogonally directed current sources. Four parameters must be determined for each source: 1 for position (the compartment number), and 3 for magnitude and orientation (magnitude in each direction). This is a reduction from the 6 required for the unconstrained case. The major advantage of this approach, however, is not the 33% parameter reduction, but rather the ability to calculate orientation from linear regression on subset vectors in a table of current density and MEG distributions produced by each candidate source. The method unambiguously finds the global least-squares explanation of the data, given the hypothesized model order and the constraints of possible source regions. Even with the simplification from non-linear least-squares to linear least-squares, combinatorial considerations still make the analysis difficult. The model order must be high enough to represent the data well; specifically, no sources should actually represent multiple sources that are sufficiently scattered to be in different functional areas (as defined by the compartmentalization). Table-driven source modeling, employing "Divide-and-Conquer" subset-selection procedures, is used to make the computations feasible, FIG. 12.

For each time point in an interval with a stable between-channel covariance pattern, subset-selection techniques are used to find the best N sets of up to 12 (depending on the number of EEG and/or MEG channels used) hypothesized sources which best produce the observed EEG and/or MEG spatiotemporal patterns, e.g., many sets of 6 hypothesized sources, many sets of 5 hypothesized sources, etc. Subset selection is accomplished by a successive approximation algorithm which iteratively reduces the size of candidate compartments. For instance, an exhaustive search is conducted for the best subset of up to six sources out of 50 compartments consisting of combined adjacent pairs from the original compartmentalization. The subset chosen can best produce the observed current density pattern, with the error weighted to emphasize those channels with larger covariances with other channels. All subsets of up to size 6 (for the 50 compartment case) are computed for each of the decimated time points in a covariance interval. The choice of 6 is determined by the maximum number of subsets which can reasonably be regressed on with current computing resources (roughly 2 msec per regression on a 2-CPU Masscomp 5700 yields 2,300,000 possible subset evaluations in approximately 77 minutes). Identification of 6 sources requires evaluation of 24 parameters. One hundred twenty-eight to 256 electric data points taken from high SNR averages is sufficient for this purpose. Higher numbers of sources may be evaluated by starting with a smaller number of larger compartments. In either case, succeeding steps repeat the subset selection to identify smaller volumes.

As a methodological check, unconstrained nonlinear least-squares methods are used to locate the best single dipole to explain the variance of the observed potential distribution. This dipole should be located at the center of gravity of the linear least-squares solution.

4. *Compartmentalized brain model.* The purpose of the brain model is to define the loci of possible candidate sources for the source localization analysis. The following steps are required:

a. Reconstruct a 3-dimensional computer graphic of the brain from MRI images.

b. Scale the brain to standard coordinates based on the distance between the anterior and posterior commisures.

c. Form a uniform grid on the cortical surface with node points, taken as a subset from the finite-difference resistive model, approximately 2.0-cm apart. The surface of the grid conforms to the gross contour of the cortical surface but does not follow the foldings into the sulci, except for the longitudinal and sylvian fissures and central sulcus.

d. At each node point, determine the 3-dimensional coordinates of the point halfway from the surface to the deepest sulcus, along the normal projection below the surface (approximately 1.5 cm). This point is the location of a candidate equivalent dipole source which could be modeled by injecting current at this point in the resistive network. This equivalent dipole represents the resultant vector of all the dipole generators in a volume aligned normal to the surface of the grid, with approximately 1.5-cm radius and 1.5-cm depth. Because of the likelihood of cortical folding within this volume, the equivalent dipole may have any orientation. Therefore 4 parameters are required to specify each equivalent dipole: 1 to identify the node, and 1 for current strength in each of the 3 coordinate directions. Roughly 90 such candidate equivalent dipole sources are required to adequately sample both cortical hemispheres with 3-cm node separation.

e. In addition to the candidate cortical sources, select a set of candidate subcortical source structures. Most subcortical locations are excluded a priori because on theoretical grounds they could not produce a discernible scalp potential or magnetic field. Prime candidates are telencephalic or diencephalic areas with structures which could produce an open field of potential. These include hippocampus, lateral geniculate bodies, ventroposterior and ventrolateral thalamic nuclei.

f. Determine the 3-dimensional locations of the subcortical candidate sources from the MRIs. Most of the candidate structures are modeled by one equivalent dipole. The hippocampus, because of its geometry, requires three separate dipoles to represent its various sub-regions. Thus, in all, there are a total of roughly 102 candidate sources.

5. *Determining the Number of Sources.* As with all regression problems, the correct parameterization is critical to a model that is generalizable and sufficiently represents the sources of variance in the data. The configuration of the scalp potential field tends to remain relatively stable for fairly long periods (50–100 msec or more), followed by brief chaotic transitions, followed by new relatively extended stable configurations. Therefore, there is imposed a maximum slope condition on the dipole solutions.

The stability of each solution for multiple dipoles is examined over such intervals. Over-parameterized configurations are likely to change radially over neighboring time points. A smoothness criterion is applied using a dynamic programming procedure to minimize error variance and between-sample variance over the interval. Under-parameterized configurations leave residuals (unexplained normal current densities and magnetic fields) which have significant topographic structure. A smoothness parameter weighting the significance of between-sample variance is perturbed to produce different solution model order trajectories over the chosen analysis interval.

6. *Cross-validation.* The resulting time-varying models are tested on an independent data set (the original ensemble of single trials is randomly split into 2 groups and subaverages formed). Squared error measures over the test set can be expected to increase for unrealistically large model orders with parameters determined from the training set.

The principal criteria for assessment of a particular multiple source solution are: (1) it should make sense. A source pattern should be consistent with prior neuroanatomical and neurophysiological knowledge, i.e., the location of sensory and motor sources should be correct; (2) it should produce an increase in signal-to-noise ratio, where the signal is measured by the significance of hypothesis tests of the between-channel covariance and the noise is measured from a noise distribution of covariance; (3) lower-order solutions (such as a single dipole) should be located at the center of gravity of clusters of the multiple source solution; (4) the source model should be a good representation (i.e., have low residual variance) for an independent set of test data.

Numerical simulations are conducted to determine an error criterion for the candidate selection process. All smoothness and cross-validation tests are conducted on a large number of candidate source combinations that fall within the error criterion of the minimum error subset. This is a safeguard against gross errors caused by incorrect choices in the initial steps of the successive approximation search. The simulations also provide a measure of the spatial resolving power of the instrument for each particular brain topology. In particular, statistics evaluated in a Monte Carlo simulation of position errors provide a confidence interval for source localization results.

What is claimed is:

1. A method to display the location and inter-area temporal relationships of a human subject's brain neural activity, comprising the steps of:

(i) determining and recording the three-dimensional location of selected portions of the subject's head and internal portions of the subject's brain and recording said locations using a three-dimensional anatomical scan instrument to provide anatomical location data;

(ii) positioning a plurality of at least 32 sensors external to the subject's scalp and proximate to the subject's scalp to detect analog brain neural activity detectable proximate to the surface of the scalp;

(iii) determining the three-dimensional positions of the sensors, converting the said sensor position determinations into digital data, and storing the said sensor position digital data in computer storage means;

(iv) providing a set of predetermined stimuli to the subject;

(v) detecting the subject's analog brain signals at the sensors during delivery of said stimuli and amplifying said analog signals; converting the analog signals into digital data and storing said digital data in computer storage means;

(vi) statistically analyzing (a) the said anatomical location data, (b) the said sensor position data, and (c) said stored brain signal digital data, to provide a set of statistical indications which represent generators of brain neural activity at sites within the brain and their temporal interrelationship; and (vii) displaying said statistical indications on a three-dimensional perspective display of at least part of a human brain, the brain portions of said display corresponding in location to the brain portion locations provided by the scan instrument.

2. The method as in claim 1 wherein the location of the selected portions of the brain is obtained by scanning the brain to provide magnetic resonance images (MRI).

3. A method as in claim 1 wherein the brain wave signals are improved in their signal-noise ratio to reduce contaminants and reduce brain activity not related to said stimulus by comparing trial sets of said brain wave digital data to statistically determined norms of uncontaminated and non-stimulus related brain wave digital data in a pattern recognition classification to eliminate those data which are contaminated or which do not have strong stimulus-related brain wave signals.

4. A method as in claim 1 wherein the sensors are electrodes positioned on the internal face of a removable hat.

5. A method as in claim 1 wherein the sensors are electrodes of an electroencephalograph (EEG) system.

6. A method as in claim 1 wherein the sensors are detectors of a magnetoencephalograph (MEG) system.

7. A method as in claim 1 wherein the stimuli are automatically presented under computer program control.

8. A method as in claim 1 wherein the stimuli include a set of motor tasks to be performed by the subject.

9. A method as in claim 8 wherein the tasks include a task in which the subject must respond with left or right hands to a visual cue.

10. A method as in claim 8 wherein the subject must respond with one hand to sound and visual cues.

11. A method as in claim 1 wherein said display includes color coded lines and areas in which color of lines indicates time delays and color or areas indicates current flow through the scalp.

12. A method as in claim 1 wherein the display is a model based on the subject's brain and head.

13. A method as in claim 1 wherein the electrical brain wave digital data is processed to reduce distortion due to passage from the originating sites to the sensors, said processing including the use of a spatial deconvolution algorithm.

14. A method as in claim 1 wherein the electrical brain digital data is processed to extract source network properties using compartmentalization, subset selection, and linear least squares methods.

15. A method as in claim 1 wherein the subject performs a predetermined task consisting of a series of trials substantially involving the voluntary movement of a portion of the subject's body in response to the stimulus and the detection of the subject's brain waves continues during each trial.

16. A method as in claim 1 wherein the display is of the spatial and temporal brain wave properties of stimulus-or response-related signals, including preparation, stimulus encoding, feature-extraction, decision, response preparation, response execution, feedback-updating, and other cognitive processes.

17. A method as in claim 1 in which the display is a model of the subject's brain and head, the scan is a magnetic resonance image (MRI) and the model is based on the said subject's MRI.

18. A system to display the location and inter-area temporal relationships of a human subject's brain neural activity, comprising:

(i) a plurality of at least 32 sensors adapted to be positioned proximate the subject's scalp to detect analog brain neural activity detectable proximate to the surface of the scalp;

(ii) means for determining the three-dimensional positions of the sensors, converting the said position determinations into digital data, and storing the said position digital data in computer storage means;

(iii) means connected to said sensors for detecting and amplifying the subject's analog brain signals; converting the analog signals into brain signal digital data and storing said brain signal digital data in computer storage;

(iv) means for statistically analyzing the stored brain signal digital data to provide a set of statistical indications of brain activity representing temporal interrelationships between sensor positions;

(v) a three-dimensional perspective display means having head and brain portions for displaying said statistical indications as lines between sensor positions; where the said head and brain portions on said display means correspond in location to the sensor positions.

19. A system as in claim 18 and further including brain scan means to determine and record the three-dimensional location of internal portions of the subject's brain, wherein the brain scan means is a magnetic resonance image (MRI) system.

20. A system as in claim 18 and including a pattern recognition classification means to eliminate those data set trials which do not have strong stimulus-related brain wave signals.

21. A system as in claim 18 and including a removable hat on which are mounted at least 32 of said sensors.

22. A system as in claim 18 and including a computer program control means to automatically present said stimuli.

23. A system as in claim 18 wherein the display is a model based on the subject's brain.

24. A system as in claim 18 wherein the sensors are electrodes of an electroencephalograph (EEG) system.

25. A system as in claim 18 wherein the sensors are detectors of a magnetoencephalograph (MEG) system.

26. A method as in claim 18 wherein the electrical brain wave digital data is processed to extract source network properites using compartmentalization, subset selection, and linear least squares methods.

27. A system to display the location and inter-area temporal relationships of a human subject's brain neural activity, comprising:

(i) brain scan means to determine and record the three-dimensional location of selected internal portions of the subject's brain and head by viewing said selected brain portions in a three-dimensional scan;

(ii) a plurality of at least 32 sensors adapted to be positioned proximate the subject's scalp to detect analog brain neural activity detectable proximate to the surface of the scalp;

(iii) means for determining the three-dimensional positions of the sensors, converting the said position determinations into digital data, and storing the said position digital data in computer storage means;

(iv) means for providing a set of predetermined stimuli to the subject;

(v) means connected to said sensors for detecting and amplifying the subject's analog brain signals which are responsive to said stimuli, converting the analog signals into brain signal digital data and storing said brain signal digital data in computer storage;

(vi) means for statistically analyzing the stored brain signal digital data to provide a set of statistical indications of brain activity representing temporal interrelationships between sensor positions; and (vii) a three-dimensional perspective display means having head and brain portions for displaying said statistical indications as lines between sensor positions; wherein the said head and brain portions on said display means correspond in location to the sensor positions.

28. A system as in claim 27 wherein the sensors are electrodes of an electroencephalograph (EEG) system.

29. A system as in claim 27 wherein the sensors are detectors of a magnetoencephalograph (MEG) system.

30. A method as in claim 27 wherein the electrical brain wave digital data is processed to extract source network properties using compartmentalization, subset selection, and linear least squares methods.

31. A system as in claim 27 wherein the brain scan means is a magnetic resonance image (MRI) system.

32. A system as in claim 27 and including a pattern recognition classification means to eliminate those data set trials which do not have strong stimulus-related brain wave signals.

33. A system as in claim 27 wherein said sensors are mounted on a removable hat.

34. A system as in claim 27 and including a computer program control means to automatically present said stimuli.

35. A system as in claim 27 wherein the display is a model based on the subject's brain.

* * * * *